United States Patent [19]

Roscher et al.

[11] 4,219,500
[45] Aug. 26, 1980

[54] PROCESS FOR THE MANUFACTURE OF N,N'-DIACETYLETHYLENE DIAMINE

[75] Inventors: Gunter Roscher; Wilfried Pressler, both of Kelkheim, Fed. Rep. of Germany

[73] Assignee: Hoechst Aktiengesellschaft, Frankfurt am Main, Fed. Rep. of Germany

[21] Appl. No.: 53,033

[22] Filed: Jun. 28, 1979

[30] Foreign Application Priority Data

Jun. 30, 1978 [DE] Fed. Rep. of Germany ....... 2828765

[51] Int. Cl.$^2$ ............................................ C07C 103/44
[52] U.S. Cl. .......................... 260/561 R; 260/561 A; 260/561 K
[58] Field of Search ........... 260/561 R, 561 A, 561 K

[56] References Cited

U.S. PATENT DOCUMENTS

| | | | |
|---|---|---|---|
| 3,223,732 | 12/1965 | Viveen et al. ................... | 260/561 R |
| 3,539,629 | 11/1970 | Mackellar et al. ............... | 260/561 R |
| 3,824,286 | 7/1974 | Grimmelikhoysen ........... | 260/561 R |
| 3,824,287 | 7/1974 | Matthias et al. ................. | 260/561 R |
| 3,886,212 | 5/1975 | Kunstle et al. .................. | 260/561 R |

FOREIGN PATENT DOCUMENTS 1378303 12/1974 United Kingdom .
1383583 2/1975 United Kingdom .

*Primary Examiner*—Arthur P. Demers
*Attorney, Agent, or Firm*—Curtis, Morris & Safford

[57] ABSTRACT

N,N'-Diacetylethylene diamine (DAED) is produced by first adding the stoichiometric amount of acetic acid (2 mols per mol of ethylene diamine) at least partially in the form of aqueous acetic acid to ethylene diamine, distilling off in a second step the water contained in the reaction mixture, adding acetic acid in excess to the remaining product, distilling off the aqueous acetic acid formed and recycling it into the first process step. The DAED remains as sump product after distillation of the acetic acid.

1 Claim, No Drawings

PROCESS FOR THE MANUFACTURE OF N,N'-DIACETYLETHYLENE DIAMINE

This invention relates to a process for the manufacture of N,N'-diacetylethylene diamine (DAED) from ethylene diamine and acetic acid. The reaction proceeds with splitting off of water according to the equation

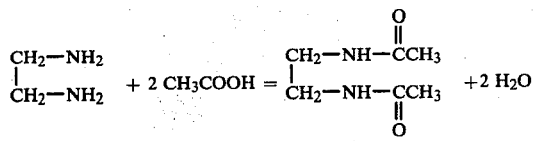

In Example 1 of SU-PS 180,605 (cf. Chem. Abstracts 69, 36 131 g (1968)) it has been proposed to prepare DAED by reacting ethylene diamine with an at least stoichiometric amount of acetic acid (in the form of glacial acetic acid or as a 50 to 95% aqueous solution) at elevated temperature while distilling off water.

According to DE-AS 2,118,282 DAED is produced continuously by adding ethylene diamine and acetic acid in a proportion by weight of 1:2 to 1:3 to a melt of DAED at a temperature of 140° to 215° C., continuously distilling off the excess amount of acetic acid and the water formed and withdrawing the DAED formed in the same measure as it is synthesized.

In DE-AS 2,133,458 it is disclosed that the formation of a possibly cyclic by-product can be suppressed in the discontinuous manufacture of DAED from ethylene diamine and acetic acid in a proportion by weight of 1:2 to 1:2.5 by starting the removal of water at an alkalinity of the reaction mixture of 50 to 10% of the initial value.

A uniform product is, however, not obtained with the use of stoichiometric amounts of acetic acid (i.e. 2 mols for each mol of ethylene diamine) (cf. Comparative Example). Acetic acid rather distills off together with the reaction water formed and the remaining reaction product has an alkaline reaction. To obtain pure DAED it is, therefore, necessary to use acetic acid in excess. This is the reason why the two specifications mentioned above, i.e. DE-AS 2,118,282 and DE-AS 2,133,458, indicate the use of an excess amount of acetic acid as being preferred. If, however, more than a stoichiometric amount of acetic acid is added to ethylene diamine, the acetic acid in excess must be removed by distillation from the DAED formed once the reaction is complete. The acetic acid distilled off is, of course, diluted by the reaction water that likewise distills off.

It is possible to recover concentrated acetic acid by distillative separation of the water, but this operation requires high technical expenditure (cf. Ullmann's Encycl. der technischen Chemie, volume 11, page 65 (1976)).

It is the object of the present invention to produce DAED from ethylene diamine and acetic acid in such a manner that the excess amount of acetic acid required for the synthesis of a pure product can be recycled without an expensive acetic acid-water separation being necessary.

The present invention, therefore, provides a process for the manufacture of N,N'-diacetylethylene diamine from ethylene diamine and acetic acid, which comprises (a) adding the stoichiometrically required amount of acetic acid at least partially in the form of aqueous acetic acid to ethylene diamine, (b) distilling off at least partially the water contained in the reaction mixture, (c) adding an excess amount of acetic acid to the remaining product, (d) heating the reaction mixture to distill off the aqueous acetic acid formed and withdrawing the N,N'-diacetylethylene diamine obtained as sump product, and (e) recycling the aqueous acetic acid distilled off into step a) of the process.

In this manner the dilute acetic acid distilled off in step (d) is re-used in step (a). In addition, fresh acetic acid is added in step a) in such an amount that the stoichiometrically required amount of acetic acid is present. Fresh acetic acid can be added in dilute or in concentrated form, preferably, however, it is added as substantially anhydrous acetic acid as usual in industry. The ethylene diamine is likewise used preferably in industrial grade anhydrous form. By the expression "stoichiometrically required amount" 2 mols of acetic acid are meant for 1 mol of ethylene diamine.

Owing to the fact that in step (a) only the stoichiometrically required amount of acetic acid is used, the distilling off of water in step (b) includes no separation of acetic acid from water since the acetic acid is bound to the ethylene diamine and, therefore, cannot distill over. The water distilled off originates (1) from the recycled aqueous acetic acid which contains the reaction water formed in step (c) of the previous cycle and (2) from the dilute fresh acetic acid optionally used in step (a). It is preferred, of course, to distill off the water in step (b) as substantially as possible to avoid an enrichment of water in the reaction mixture. It is not necessary, however, to distill off the total amount of water, a small portion thereof may remain in the reaction mixture, for example ¼ mol of water per mol of ethylene diamine, which can be recycled. In other words, in step (b) of one cycle preferably the total amount of reaction water )2 mols per mol of DAED) of the previous cycle and the water, if any, introduced in step (a) with the fresh aqueous acetic acid are distilled off. In general, the distillation is carried out at a temperature of from 60° to 140° C. at atmospheric pressure or reduced pressure.

In step (c) the product remaining after having distilled off the water is admixed with an excess amount of acetic acid, preferably 0.1 to 1 mol for each mol of ethylene diamine used in step (a). In general, this acetic acid should contain as little water as possible. It proved advantageous to use substantially anhydrous acetic acid as usual in industry.

The reaction mixture is preferably heated in step (d) to 140° to 220° C. whereby the excess amount of acetic acid, diluted by the reaction water formed, the residual water, if any, which has not been distilled off in step (b) and the water possibly introduced in step (c) is distilled off together with the excess amount of acetic acid. The DAED formed is withdrawn from the sump. The diluted acetic acid obtained is recycled into step (a).

The process according to the invention has the advantage that a high yield of N,N'-diacetylethylene diamine having a very high purity is obtained without a complicate working up of aqueous acetic acid being necessary. The DAED obtained can be further reacted without purification to give N,N,N',N'-tetraacetylethylene diamine which is used as additive for detergents. This reaction is described, for example, in U.S. Pat. No. 3,539,629.

The process according to the invention can be carried out either continuously or discontinuously. In the continuous process at least 2 and preferably 3 series-connected reaction zones, for example a cascade consisting of 3 vessels with stirrer are used. It is preferably carried out as follows:

In the first vessel ethylene diamine is neutralized with fresh, industrial grade anhydrous acetic acid and aqueous recycled acetic acid, at a temperature of from 60° to 140° C. in a total molar proportion of ethylene diamine to acetic acid of 1:2. In this zone the temperature should be chosen in such a manner that 2 mols of water continuously distill off from the neutralization mixture per mol of ethylene diamine.

The sump product of the first vessel is continuously transferred into a second vessel with stirrer in which the splitting off of water is started by heating to 140° to 180° C., preferably 150° to 170° C. with continuous addition of 0.1 to 1 mol of acetic acid, preferably 0.3 to 0.5 mol, per mol of ethylene diamine used. The splitting off of water is completed in a third vessel with stirrer at a temperature of from 180° to 220° C., preferably 190° to 210° C. The reaction water is continuously distilled off from vessels 2 and 3 together with the acetic acid in excess. The aqueous acetic acid obtained in this manner is recycled into the first vessel with stirrer. Pure N,N'-diacetylethylene diamine is continuously withdrawn from the third vessel with stirrer in the form of a melt; it solidifies on cooling. It is likewise possible, of course, to use a cascade composed of more than three vessels.

For discontinuous operation it is preferred to charge a vessel with stirrer with the mixture of fresh, industrial grade anhydrous acetic acid and aqueous recycled acetic acid and the stoichiometric amount of ethylene diamine (molar proportion of ethylene diamine to total acetic acid 1:2) is added. The temperature of the mixture rises due to the heat of neutralization. Next, 2 mols of water per mol of ethylene diamine are distilled off at atmospheric pressure or reduced pressure and at 60° to 140° C.

0.1 to 1 Mol, preferably 0.4 to 0.6 mol of acetic acid is then added for each mol of ethylene diamine. The reaction mixture is heated to 140° to 220° C., preferably 160° to 200° C., and the reaction water is distilled off together with the excess amount of acetic acid at atmospheric pressure or under reduced pressure. The aqueous acetic acid obtained is reused for the following batch. Pure and practically colorless N,N'-diacetylethylene diamine is obtained as sump product.

In the continuous as well as in the discontinuous process an inert gas such as nitrogen should be used in all reaction vessels.

The following examples illustrate the invention.

EXAMPLE 1: (continuous operation)

The cascade used consists of 3 vessels with stirrer each having a capacity of 2 liters. The first vessel is charged per hour with 900 g (15 mols) of industrial grade anhydrous ethylene diamine (purity over 99%), 1,500 g (25 mols) of industrial grade anhydrous acetic acid (water content less than 0.1%) and 910 g of 33% aqueous recycled acetic acid (300 g of pure acetic acid=5 mols). In the first vessel a temperature of 135° C. is adjusted, whereupon 535 g of water containing less than 1% by weight of acetic acid distill over per hour.

The overflow from the first vessel is passed into the second vessel which is charged additionally with 360 g (6 mols) per hour of industrial grade anhydrous acetic acid. In the second vessel a temperature of 165° C. is adjusted. The acetic acid-water mixture distilling off is collected in a receiver.

The overflow from the second vessel is passed into the third vessel from which the residual acetic acid-water mixture is distilled off at 195° C. and collected in the aforesaid receiver.

In the receiver 910 g of 33% aqueous acetic acid are obtained per hour, which are recycled into the first vessel. From the overflow of the third vessel 2,225 g per hour of N,N'-diacetylethylene diamine still containing 2.5% by weight of acetic acid and 0.5% by weight of water are obtained, which corresponds to a quantitative yield. The solidified product is practically colorless and melts at 174° C.

EXAMPLE 2: (discontinuous operation)

A vessel with stirrer is charged with 1,860 g (31 mols) of industrial grade, anhydrous acetic acid (water content less than 0.1%) and 1,350 g of 40% recycled aqueous acetic acid (540 g=9 mols of pure acetic acid). Then 1,200 g (20 mols) of industrial grade, anhydrous ethylene diamine (purity over 99%) are added over a period of 30 minutes whereupon the temperature rises to 125° C. and the mixture boils with reflux. The pressure is slowly reduced to 80 millibar and, at a sump temperature of 75° to 105° C., 700 g of water having an acetic acid content of less than 1% by weight are distilled off. Next, 600 g (10 mols) of industrial grade, anhydrous acetic acid are added, the reaction mixture is slowly heated to 175° C. under 80 millibar and the reaction water formed is distilled off together with the excess amount of acetic acid. After 3 hours, 1,350 g of 40% aqueous acetic acid are distilled off, which are reused in the following batch. As sump 2,960 g of N,N'-diacetylethylene diamine still containing 2% by weight of acetic acid and 1% by weight of water are obtained, corresponding to a quantitative yield. The solidified product is practically colorless and melts at 172° C.

COMPARATIVE EXAMPLE: (with the use of a stoichiometric amount of acetic acid)

A vessel with stirrer is charged with 2,400 g (40 mols) of industrial grade, anhydrous acetic acid (water content less than 1.0%) and 1,200 g (20 mols) of industrial grade anhydrous ethylene diamine are added over a period of 60 minutes. The temperature rises to 140° C. and the reaction mixture boils with reflux. The mixture is stirred for 30 minutes under reflux and then the reaction water is distilled off at a sump temperature of up to 180° C. To complete the water removal, the pressure is slowly reduced to 80 millibar at the said temperature. After 3.5 hours, a total amount of 710 g of water have distilled off containing 4% by weight of acetic acid.

As sump there remain 2,890 g of crude N,N'-diacetylethylene diamine still containing 1% by weight of water. The solidified product starts to melt at about 90° C. and an aqueous solution thereof has an alkaline reaction.

What is claimed is:

1. Process for the manufacture of N,N'-diacetylethylene diamine from ethylene diamine and acetic acid, which comprises
   (a) adding the stoichiometrically required amount of acetic acid at least partially in the form of aqueous acetic acid to ethylene diamine,
   (b) distilling off at least partially the water contained in the reaction mixture,
   (c) adding an excess amount of acetic acid to the remaining product,
   (d) heating the reaction mixture to distill off the aqueous acetic acid formed and withdrawing the N,N'-diacetylethylene diamine obtained as sump product, and
   (e) recycling the aqueous acetic acid distilled off into step (a) of the process.

* * * * *